(12) United States Patent
Andrews et al.

(10) Patent No.: US 7,226,744 B2
(45) Date of Patent: Jun. 5, 2007

(54) ASSAYS FOR TERT PROMOTER MODULATORY AGENTS USING A TELOMERASE STRUCTURAL RNA COMPONENT

(75) Inventors: William H. Andrews, Reno, NV (US); Laura Briggs, Reno, NV (US); Lancer K. Brown, Sparks, NV (US); Christopher A. Foster, Reno, NV (US); Mieczyslaw A. Piatyszek, Morgan Hill, CA (US)

(73) Assignee: Sierra Sciences, Inc., Reno, NV (US)

( * ) Notice: Subject to any disclaimer, the term of this patent is extended or adjusted under 35 U.S.C. 154(b) by 0 days.

(21) Appl. No.: 11/085,872

(22) Filed: Mar. 21, 2005

(65) Prior Publication Data

US 2006/0154266 A1 Jul. 13, 2006

Related U.S. Application Data

(60) Provisional application No. 60/643,649, filed on Jan. 12, 2005.

(51) Int. Cl.
*C12Q 1/68* (2006.01)
(52) U.S. Cl. .......................................... 435/6; 435/455
(58) Field of Classification Search ............... 536/23.1, 536/24.1; 435/6, 455, 320.1, 325
See application file for complete search history.

(56) References Cited

U.S. PATENT DOCUMENTS

| | | | |
|---|---|---|---|
| 5,972,605 | A | 10/1999 | Villeponteau et al. |
| 6,610,839 | B1 | 8/2003 | Morin et al. |
| 6,664,046 | B1 | 12/2003 | Chang et al. |
| 2004/0072787 | A1 | 4/2004 | Morin et al. |

FOREIGN PATENT DOCUMENTS

| | | |
|---|---|---|
| WO | WO 02/16657 | 2/2002 |
| WO | WO 02/16658 | 2/2002 |
| WO | WO 02/070668 | 9/2002 |
| WO | WO 02/072787 | 9/2002 |
| WO | WO 02/090570 | 11/2002 |
| WO | WO 02/090571 | 11/2002 |
| WO | WO 02/101010 | 12/2002 |
| WO | WO 03/000916 | 1/2003 |
| WO | WO 03/016474 | 2/2003 |

OTHER PUBLICATIONS

Ducrest et al. Oncogene. 2002; 21:541-552.*
Kim et al. PNAS 2001; 98:7982-87.*
Li et al. Canc. Res. 2004; 64:4833-40.*
Wang et al. Oncogene. 2002; 21:3517-24.*
Won et al. PNAS. 2004; 101:11328-33.*
Feng et al. 1995; 269:1236-41.*
Marusic et al. (Mol. Cell Biol., 1997, 17(1): 6394-6401.*
Li et al. "Rapid Inhbition of Cancer Cell Growth Induced by Lentiviral Delivery and Expression of Mutant Template Telomerase RNA and Anti-Telomerase Short-Interfering RNA," (2004) Cancer Research, 64:4833-4840.

* cited by examiner

*Primary Examiner*—James Ketter
(74) *Attorney, Agent, or Firm*—Bret E. Field; Bozicevic, Field & Francis LLP; David C. Scherer

(57) ABSTRACT

Methods and compositions for assaying an agent for TERT promoter modulatory activity are provided. In the subject methods, an agent is contacted with a cell comprising a mutant telomerase structural RNA component (TR) that results in a detectable phenotype in the presence of telomerase reverse transcriptase (TERT). Also provided are compositions, systems and kits thereof, as well as devices, that find use in practicing the subject methods. The subject invention finds use in assaying agents for TERT promoter modulatory activity, such as in a high throughput format.

22 Claims, No Drawings

SEQUENCE LISTING

<160> NUMBER OF SEQ ID NOS: 2

<210> SEQ ID NO 1
<211> LENGTH: 15418
<212> TYPE: DNA
<213> ORGANISM: human

<400> SEQUENCE: 1

```
gcggccgcga gctctaatac gactcactat agggcgtcga ctcgatcaat ggaagatgag      60
gcattgccga agaaaagatt aatggatttg aacacacagc aacagaaact acatgaagtg     120
aaacacagga aaaaaagat aaagaaacga aaagaaaagg gcatcagtga gcttcagcag     180
aagttccatc ggccttacat atgtgtaagc agaggccctg taggagcaga ggcaggggga     240
aaatacttta agaaataatg tctaaaagtt tttcaaatat gaggaaaaac ataaaaccac     300
agatccaaga agctcaacaa aacaaagcac aagaaacagg aagaaattaa aagttatatc     360
acagtcaaat tgctgaaaac cagcaacaaa gagaatatct taagagtatc agaggaaaag     420
agattaatga caggccaaga aacaatgaaa acaatacaga tttcttgtag gaaacacaag     480
acaaaagaca tttttaaaa ccaaaaggaa aaaaaatgct acattaaaat gttttttacc     540
cactgaaagt atatttcaaa acatatttta ggccaggctt ggtggctcac acctgtaatc     600
ccagcacttt gggaggccaa ggtgggtgga tcgcttaagg tcaggagttc gagaccagcc     660
tggccaatat agcgaaaccc catctgtact aaaaacacaa aaattagctg ggtgtggtga     720
cacatgcctg taatcccagg tactcaggag gctaaggcag gagaattgct tgaactggga     780
ggcagaggtg gtgagccaag attgcaccag tgcactccag ccttggtgac agagtgaaac     840
tccatctcaa aaacaaacaa acaaaataca tatacataaa tatatatgca catatatata     900
catatataaa tatatataca catatataaa tctatataca tatatacata tatacacata     960
tataaatcta tatacatata tatacatata taatatattt acatatataa atatatacat    1020
atataaatat acatatataa atacatatat aaatatacat atataaatat acatatataa    1080
```

-continued

```
atatacatat ataaatatat acatatataa atatacatat ataaatatat atacatatat    1140
aaatatataa atatacaagt atatacaaat atatacatat ataaatgtat atacgtatat    1200
acatatatat ataaatatat aaaaaaactt ttggctgggc acctttccaa atctcatggc    1260
acatataagt ctcatggtaa cctcaaataa aaaacatat aacagataca ccaaaaataa    1320
aaaccaataa attaaatcat gccaccagaa gaaattacct tcactaaaag gaacacagga    1380
aggaaagaaa gaaggaagag aagaccatga acaaccaga aaacaaacaa caaaacagca    1440
ggagtaattc ctgacttatc aataataatg ctgggtgtaa atggactaaa ctctccaatc    1500
aaaagacata gagtggctga atggacgaaa aaaacaagac tcaataatct gttgcctaca    1560
agaatatact tcacctataa agggacacat agactgaaaa taaaaggaag gaaaaatatt    1620
ctatgcaaat ggaaaccaaa aaaagaacag aactagctac acttatatca gacaaaatag    1680
atttcaagac aaaagtaca aaagagaca aagtaattat ataataataa agcaaaaaga    1740
tataacaatt gtgaatttat atgcgcccaa cactgggaca cccagatata tacagcaaat    1800
attattagaa ctaaggagag agagagatcc ccatacaata atagctggag acttcaccccc   1860 gcttttagca ttggacagat catccagaca gaaaatcaac caaaaaattg gacttaatct    1920
ataatataga acaaatgtac ctaattgatg tttacaagac atttcatcca gtagttgcag    1980
aatatgcatt ttttcctcag catatggatc attctcaagg atagaccata tattaggcca    2040
cagaacaagc cattaaaaat tcaaaaaaat tgagccaggc atgatggctt atgcttgtaa    2100
ttacagcact ttggggaggg tgaggtggga ggatgtcttg agtacaggag tttgagacca    2160
gcctgggcaa aatagtgaga ccctgtctct acaaactttt tttttttaatt agccaggcat    2220 agtggtgtgt gcctgtagtc ccagctactt aggaggctga agtgggagga tcacttgagc    2280
ccaagagttc aaggctacgg tgagccatga ttgcaacacc acacaccagc cttggtgaca    2340
gaatgagacc ctgtctcaaa aaaaaaaaaa aaaattgaaa taatataaag catcttctct    2400
ggccacagtg gaacaaaacc agaaatcaac aacaagagga attttgaaaa ctatacaaac    2460
acatgaaaat taaacaatat acttctgaat aaccagtgag tcaatgaaga aattaaaaag    2520
gaaattgaaa aatttattta agcaaatgat aacggaaaca taacctctca aaacccacgg    2580
tatacagcaa aagcagtgct aagaaggaag tttatagcta taagcagcta catcaaaaaa    2640
gtagaaaagc caggcgcagt ggctcatgcc tgtaatccca gcactttggg aggccaaggc    2700
gggcagatcg cctgaggtca ggagttcgag accagcctga ccaacacaga gaaaccttgt    2760
cgctactaaa aatacaaaat tagctgggca tggtggcaca tgcctgtaat cccagctact    2820
cgggaggctg aggcaggata accgcttgaa cccaggaggt ggaggttgcg gtgagccggg    2880
attgcgccat tggactccag cctgggtaac aagagtgaaa ccctgtctca agaaaaaaaa    2940
aaaagtagaa aaacttaaaa atacaaccta atgatgcacc ttaaagaact agaaaagcaa    3000
gagcaaacta aacctaaaat tggtaaaaga aagaaataa taaagatcag agcagaaata    3060
aatgaaactg aaagataaca atacaaaaga tcaacaaaat taaaagttgg tttttttgaaa   3120 agataaacaa aattgacaaa cctttgccca gactaagaaa aaaggaaaga agacctaaat    3180
aaataaagtc agagatgaaa aaagagacat tacaactgat accacagaaa ttcaaaggat    3240
cactagaggc tactatgagc aactgtacac taataaattg aaaaacctag aaaaaataga    3300
taaattccta gatgcataca acctaccaag attgaaccat gaagaaatcc aaagcccaaa    3360
cagaccaata acaataatgg gattaaagcc ataataaaaa gtctcctagc aaagagaagc    3420
ccaggaccca atggcttccc tgctggattt taccaatcat ttaaagaaga atgaattcca    3480
```

-continued

| | |
|---|---|
| atcctactca aactattctg aaaaatagag gaaagaatac ttccaaactc attctacatg | 3540 |
| gccagtatta ccctgattcc aaaaccagac aaaaacacat caaaaacaaa caaacaaaaa | 3600 |
| aacagaaaga aagaaaacta caggccaata tccctgatga atactgatac aaaaatcctc | 3660 |
| aacaaaacac tagcaaacca aattaaacaa caccttcgaa agatcattca ttgtgatcaa | 3720 |
| gtgggattta ttccagggat ggaaggatgg ttcaacatat gcaaatcaat caatgtgata | 3780 |
| catcatccca acaaaatgaa gtacaaaaac tatatgatta tttcacttta tgcagaaaaa | 3840 |
| gcatttgata aaattctgca cccttcatga taaaaaccct caaaaaacca ggtatacaag | 3900 |
| aaacatacag gccaggcaca gtggctcaca cctgcgatcc cagcactctg ggaggccaag | 3960 |
| gtgggatgat tgcttgggcc caggagtttg agactagcct gggcaacaaa atgagacctg | 4020 |
| gtctacaaaa aacttttttta aaaaattagc caggcatgat ggcatatgcc tgtagtccca | 4080 |
| gctagtctgg aggctgaggt gggagaatca cttaagccta ggaggtcgag gctgcagtga | 4140 |
| gccatgaaca tgtcactgta ctccagccta gacaacagaa caagacccca ctgaataaga | 4200 |
| agaaggagaa ggagaaggga gaaggaggg agaagggagg aggaggagaa ggaggaggtg | 4260 |
| gaggagaagt ggaagggaa ggggaaggga aagaggaaga agaagaaaca tatttcaaca | 4320 |
| taataaaagc cctatatgac agaccgaggt agtattatga ggaaaactg aaagcctttc | 4380 |
| ctctaagatc tggaaaatga caagggccca cttttcaccac tgtgattcaa catagtacta | 4440 |
| gaagtcctag ctagagcaat cagataagag aaagaaataa aaggcatcca aactggaaag | 4500 |
| gaagaagtca aattatcctg tttgcagatg atatgatctt atatctggaa aagacttaag | 4560 |
| acaccactaa aaaactatta gagctgaaat ttggtacagc aggatacaaa atcaatgtac | 4620 |
| aaaaatcagt agtatttcta tattccaaca gcaaacaatc tgaaaagaa accaaaaaag | 4680 |
| cagctacaaa taaaattaaa cagctaggaa ttaaccaaag aagtgaaaga tctctacaat | 4740 |
| gaaaactata aaatattgat aaaagaaatt gaagagggca caaaaaaaga aaagatattc | 4800 |
| catgttcata gattggaaga ataaatactg ttaaaatgtc catactaccc aaagcaattt | 4860 |
| acaaattcaa tgcaatccct attaaaatac taatgacgtt cttcacagaa atagaagaaa | 4920 |
| caattctaag atttgtacag aaccacaaaa gacccagaat agccaaagct atcctgacca | 4980 |
| aaaagaacaa aactggaagc atcacattac ctgacttcaa attatactac aaagctatag | 5040 |
| taacccaaac tacatggtac tggcataaaa acagatgaga catggaccag aggaacagaa | 5100 |
| tagagaatcc agaaacaaat ccatgcatct acagtgaact catttttgac aaaggtgcca | 5160 |
| agaacatact ttggggaaaa gataatctct tcaataaatg gtgctggagg aactggatat | 5220 |
| ccatatgcaa ataacaata ctagaactct gtctctcacc atatacaaaa gcaaatcaaa | 5280 |
| atggatgaaa ggcttaaatc taaaacctca aactttgcaa ctactaaaag aaaacaccgg | 5340 |
| agaaactctc caggacattg gagtgggcaa agacttcttg agtaattccc tgcaggcaca | 5400 |
| ggcaaccaaa gcaaaaacag acaaatggga tcatatcaag ttaaaaagct tctgcccagc | 5460 |
| aaaggaaaca atcaacaaag agaagagaca acccacagaa tgggagaata tatttgcaaa | 5520 |
| ctattcatct aacaaggaat taataaccag tatatataag gagctcaaac tactctataa | 5580 |
| gaaaacaccc taataagctg attttcaaaa ataagcaaaa gatctgggta gacatttctc | 5640 |
| aaaataagtc atacaaatgg caaacaggca tctgaaaatg tgctcaacac cactgatcat | 5700 |
| cagagaaatg caaatcaaaa ctactatgag agatcatctc accccagtta aaatggcttt | 5760 |
| tattcaaaag acaggcaata acaaatgcca gtgaggatgt ggataaaagg aaacccttgg | 5820 |

```
acactgttgg tgggaatgga aattgctacc actatggaga acagtttgaa agttcctcaa    5880
aaaactaaaa ataaagctac catacagcaa tcccattgct aggtatatac tccaaaaaag    5940
ggaatcagtg tatcaacaag ctatctccac tcccacattt actgcagcac tgttcatagc    6000
agccaaggtt tggaagcaac ctcagtgtcc atcaacagac gaatggaaaa agaaaatgtg    6060
gtgcacatac acaatggagt actacgcagc cataaaaaag aatgagatcc tgtcagttgc    6120
aacagcatgg ggggcactgg tcagtatgtt aagtgaaata agccaggcac agaaagacaa    6180
acttttcatg ttctccctta cttgtgggag caaaaattaa acaattgac atagaaatag    6240 aggagaatgg tggttctaga ggggtggggg acagggtgac tagagtcaac aataatttat    6300
tgtatgtttt aaaataacta aaagagtata attgggttgt ttgtaacaca agaaaggat    6360 aaatgcttga aggtgacaga taccccattt accctgatgt gattattaca cattgtatgc    6420
ctgtatcaaa atatctcatg tatgctatag atataaaccc tactatatta aaaattaaaa    6480
ttttaatggc caggcacggt ggctcatgtc cataatccca gcactttggg aggccgaggc    6540
ggtggatcac ctgaggtcag gagtttgaaa ccagtctggc caccatgatg aaaccctgtc    6600
tctactaaag atacaaaaat tagccaggcg tggtggcaca tacctgtagt cccaactact    6660
caggaggctg agacaggaga attgcttgaa cctgggaggc ggaggttgca gtgagccgag    6720
atcatgccac tgcactgcag cctgggtgac agagcaagac tccatctcaa aacaaaaaca    6780 aaaaaagaa gattaaaatt gtaattttta tgtaccgtat aaatatatac tctactatat    6840
tagaagttaa aaattaaaac aattataaaa ggtaattaac cacttaatct aaaataagaa    6900
caatgtatgt ggggtttcta gcttctgaag aagtaaaagt tatggccacg atggcagaaa    6960
tgtgaggagg gaacagtgga agttactgtt gttagacgct catactctct gtaagtgact    7020
taattttaac caaagacagg ctgggagaag ttaaagaggc attctataag ccctaaaaca    7080
actgctaata atggtgaaag gtaatctcta ttaattacca ataattacag atatctctaa    7140
aatcgagctg cagaattggc acgtctgatc acaccgtcct ctcattcacg gtgcttttt    7200 tcttgtgtgc ttggagattt tcgattgtgt gttcgtgttt ggttaaactt aatctgtatg    7260
aatcctgaaa cgaaaaatgg tggtgatttc ctccagaaga attagagtac ctggcaggaa    7320
gcaggtggct ctgtggacct gagccacttc aatcttcaag ggtctctggc caagacccag    7380
gtgcaaggca gaggcctgat gacccgagga caggaaagct cggatgggaa ggggcgatga    7440
gaagcctgcc tcgttggtga gcagcgcatg aagtgcccct tatttacgct tgcaaagatt    7500
gctctggata ccatctggaa aaggcggcca gcgggaatgc aaggagtcag aagcctcctg    7560
ctcaaaccca ggccagcagc tatgcgcgcc acccggcgt gtgccagagg gagaggagtc    7620
aaggcacctc gaagtatggc ttaaatcttt ttttcacctg aagcagtgac caaggtgtat    7680
tctgagggaa gcttgagtta ggtgccttct ttaaaacaga aagtcatgga agcacccttc    7740
tcaagggaaa accagacgcc cgctctgcgg tcatttacct ctttcctctc tccctctctt    7800
gccctcgcgg tttctgatcg ggacagagtg accccgtgg agcttctccg agcccgtgct    7860
gaggaccctc ttgcaaaggg ctccacagac ccccgccctg gagagaggag tctgagcctg    7920
gcttaataac aaactgggat gtggctgggg gcggacagcg acggcgggat tcaaagactt    7980
aattccatga gtaaattcaa cctttccaca tccgaatgga tttggatttt atcttaatat    8040
tttcttaaat ttcatcaaat aacattcagg agtgcagaaa tccaaaggcg taaaacagga    8100
actgagctat gtttgccaag gtccaaggac ttaataacca tgttcagagg gattttttcgc    8160 cctaagtact ttttattggt tttcataagg tggcttaggg tgcaagggaa agtacacgag    8220
```

```
gagaggactg ggcggcaggg ctatgagcac ggcaaggcca ccggggagag agtccccggc    8280
ctgggaggct gacagcagga ccactgaccg tcctccctgg gagctgccac attgggcaac    8340
gcgaaggcgg ccacgctgcg tgtgactcag accccatac cggcttcctg ggcccaccca    8400
cactaaccca ggaagtcacg gagctctgaa cccgtggaaa cgaacatgac ccttgcctgc    8460
ctgcttccct gggtgggtca agggtaatga agtggtgtgc aggaaatggc catgtaaatt    8520
acacgactct gctgatgggg accgttcctt ccatcattat tcatcttcac ccccaaggac    8580
tgaatgattc cagcaacttc ttcgggtgtg acaagccatg acaacactca gtacaaacac    8640
cactcttta ctaggcccac agagcacggc ccacacccct gatatattaa gagtccagga    8700
gagatgaggc tgctttcagc caccaggctg gggtgacaac agcggctgaa cagtctgttc    8760
ctctagacta gtagaccctg gcaggcactc ccccagattc tagggcctgg ttgctgcttc    8820
ccgagggcgc catctgccct ggagactcag cctggggtgc cacactgagg ccagccctgt    8880
ctccacaccc tccgcctcca ggcctcagct tctccagcag cttcctaaac cctgggtggg    8940
ccgtgttcca gcgctactgt ctcacctgtc ccactgtgtc ttgtctcagc gacgtagctc    9000
gcacggttcc tcctcacatg gggtgtctgt ctccttcccc aacactcaca tgcgttgaag    9060
ggaggagatt ctgcgcctcc cagactggcc cctctgagcc tgaacctggc tcgtggcccc    9120
cgatgcaggt tcctggcgtc cggctgcacg ctgacctcca tttccaggcg ctccccgtct    9180
cctgtcatct gccggggcct gccggtgtgt tcttctgttt ctgtgctcct ttccacgtcc    9240
agctgcgtgt gtctctgtcc gctagggtct cggggttttt ataggcatag gacggggggcg   9300
tggtgggcca gggcgctctt gggaaatgca acatttgggt gtgaaagtag gagtgcctgt    9360
cctcacctag gtcacgggc acaggcctgg ggatggagcc cccgccaggg acccgcccctt    9420
ctctgcccag cacttttctg ccccctccc tctggaacac agagtggcag tttccacaag    9480
cactaagcat cctcttccca aaagacccag cattggcacc cctggacatt tgccccacag    9540
ccctgggaat tcacgtgact acgcacatca tgtacacact cccgtccacg accgaccccc    9600
gctgtttat tttaatagct acaaagcagg gaaatccctg ctaaaatgtc ctttaacaaa    9660
ctggttaaac aaacgggtcc atccgcacgg tggacagttc ctcacagtga agaggaacat    9720
gccgtttata aagcctgcag gcatctcaag ggaattacgc tgagtcaaaa ctgccacctc    9780
catgggatac gtacgcaaca tgctcaaaaa gaaagaattt caccccatgg caggggagtg    9840
gttgggggt taaggacggt gggggcagca gctgggggct actgcacgca ccttttacta    9900
aagccagttt cctggttctg atggtattgg ctcagttatg ggagactaac catagggggag   9960
tggggatggg ggaacccgga ggctgtgcca tctttgccat gcccgagtgt cctgggcagg   10020
ataatgctct agagatgccc acgtcctgat tcccccaaac ctgtggacag aacccgcccg   10080
gccccagggc ctttgcaggt gtgatctccg tgaggaccct gaggtctggg atccttcggg   10140
actacctgca ggcccgaaaa gtaatccagg ggttctggga agaggcgggc aggagggtca   10200
gagggggggca gcctcaggac gatggaggca gtcagtctga ggctgaaaag ggagggaggg   10260
cctcgagccc aggcctgcaa gcgcctccag aagctggaaa aagcggggaa gggaccctcc   10320
acggagcctg cagcaggaag gcacggctgg cccttagccc accagggccc atcgtggacc   10380
tccggcctcc gtgccatagg agggcactcg cgctgcccctt ctagcatgaa gtgtgtgggg   10440
atttgcagaa gcaacaggaa acccatgcac tgtgaatcta ggattatttc aaaacaaagg   10500
tttacagaaa catccaagga cagggctgaa gtgcctccgg gcaagggcag ggcaggcacg   10560
```

-continued

| | | | | |
|---|---|---|---|---|
| agtgatttta | tttagctatt | ttattttatt | tacttacttt | ctgagacaga gttatgctct | 10620 |
| tgttgcccag | gctggagtgc | agcggcatga | tcttggctca | ctgcaacctc cgtctcctgg | 10680 |
| gttcaagcaa | ttctcgtgcc | tcagcctccc | aagtagctgg | gatttcaggc gtgcaccacc | 10740 |
| acacccggct | aattttgtat | ttttagtaga | gatgggcttt | caccatgttg gtcaggctga | 10800 |
| tctcaaaatc | ctgacctcag | gtgatccgcc | cacctcagcc | tcccaaagtg ctgggattac | 10860 |
| aggcatgagc | cactgcacct | ggcctattta | accattttaa | aacttccctg gctcaagtc | 10920 |
| acacccactg | gtaaggagtt | catggagttc | aatttcccct | ttactcagga gttaccctcc | 10980 |
| tttgatattt | tctgtaattc | ttcgtagact | ggggatacac | cgtctcttga catattcaca | 11040 |
| gtttctgtga | ccacctgtta | tcccatggga | cccactgcag | gggcagctgg gaggctgcag | 11100 |
| gcttcaggtc | ccagtggggt | tgccatctgc | cagtagaaac | ctgatgtaga atcagggcgc | 11160 |
| gagtgtggac | actgtcctga | atctcaatgt | ctcagtgtgt | gctgaaacat gtagaaatta | 11220 |
| aagtccatcc | ctcctactct | actgggattg | agcccttcc | ctatcccccc ccaggggcag | 11280 |
| aggagttcct | ctcactcctg | tggaggaagg | aatgatactt | tgttattttt cactgctggt | 11340 |
| actgaatcca | ctgtttcatt | tgttggtttg | tttgttttgt | tttgagaggc ggtttcactc | 11400 |
| ttgttgctca | ggctggaggg | agtgcaatgg | cgcgatcttg | gcttactgca gcctctgcct | 11460 |
| cccaggttca | agtgattctc | ctgcttccgc | ctcccatttg | gctgggatta caggcacccg | 11520 |
| ccaccatgcc | cagctaattt | tttgtatttt | tagtagagac | ggggtggg gtgggttca | 11580 |
| ccatgttggc | caggctggtc | tcgaacttct | gacctcagat | gatccacctg cctctgcctc | 11640 |
| ctaaagtgct | gggattacag | gtgtgagcca | ccatgcccag | ctcagaattt actctgttta | 11700 |
| gaaacatctg | gtctgaggt | aggaagctca | ccccactcaa | gtgttgtggt gttttaagcc | 11760 |
| aatgatagaa | ttttttatt | gttgttagaa | cactcttgat | gttttacact gtgatgacta | 11820 |
| agacatcatc | agcttttcaa | agacacacta | actgcaccca | taatactggg gtgtcttctg | 11880 |
| ggtatcagcg | atcttcattg | aatgccggga | ggcgtttcct | cgccatgcac atggtgttaa | 11940 |
| ttactccagc | ataatcttct | gcttccattt | cttctcttcc | ctcttttaaa attgtgtttt | 12000 |
| ctatgttggc | ttctctgcag | agaaccagtg | taagctacaa | cttaacttt gttggaacaa | 12060 |
| attttccaaa | ccgccccttt | gccctagtgg | cagagacaat | tcacaaacac agcccttta | 12120 |
| aaaggcttag | ggatcactaa | ggggatttct | agaagagcga | cccgtaatcc taagtattta | 12180 |
| caagacgagg | ctaacctcca | gcgagcgtga | cagcccaggg | agggtgcgag gcctgttcaa | 12240 |
| atgctagctc | cataaataaa | gcaatttcct | ccggcagttt | ctgaaagtag gaaaggttac | 12300 |
| atttaaggtt | gcgtttgtta | gcatttcagt | gtttgccgac | ctcagctaca gcatccctgc | 12360 |
| aaggcctcgg | gagacccaga | agtttctcgc | cccttagatc | caaacttgag caacccggag | 12420 |
| tctggattcc | tgggaagtcc | tcagctgtcc | tgcggttgtg | ccggggcccc aggtctggag | 12480 |
| gggaccagtg | gccgtgtggc | ttctactgct | gggctggaag | tcgggcctcc tagctctgca | 12540 |
| gtccgaggct | tggagccagg | tgcctggacc | ccgaggctgc | cctccaccct gtgcgggcgg | 12600 |
| gatgtgacca | gatgttggcc | tcatctgcca | gacagagtgc | cggggcccag ggtcaaggcc | 12660 |
| gttgtggctg | gtgtgaggcg | cccggtgcgc | ggccagcagg | agcgcctggc tccatttccc | 12720 |
| acccttctc | gacgggaccg | ccccggtggg | tgattaacag | atttgggtg gtttgctcat | 12780 |
| ggtggggacc | cctcgccgcc | tgagaacctg | caaagagaaa | tgacgggcct gtgtcaagga | 12840 |
| gcccaagtcg | cggggaagtg | ttgcagggag | gcactccggg | aggtcccgcg tgcccgtcca | 12900 |
| gggagcaatg | cgtcctcggg | ttcgtcccca | gccgcgtcta | cgcgcctccg tcctcccctt | 12960 |

-continued

| | |
|---|---|
| cacgtccggc attcgtggtg cccggagccc gacgccccgc gtccggacct ggaggcagcc | 13020 |
| ctgggtctcc ggatcaggcc agcggccaaa gggtcgccgc acgcacctgt tcccagggcc | 13080 |
| tccacatcat ggccctccc tcgggttacc ccacagccta ggccgattcg acctctctcc | 13140 |
| gctgggcccc tcgctggcgt ccctgcaccc tgggagcgcg agcggcgcgc gggcggggaa | 13200 |
| gcgcggccca gaccccggg tccgcccgga gcagctgcgc tgtcggggcc aggccgggct | 13260 |
| cccagtggat tcgcgggcac agacgcccag gaccgcgctt cccacgtggc ggagggactg | 13320 |
| gggacccggg cacccgtcct gccccttcac cttccagctc cgcctcctcc gcgcggaccc | 13380 |
| cgccccgtcc cgacccctcc cgggtccccg gcccagcccc ctccgggccc tcccagcccc | 13440 |
| tccccttcct ttccgcggcc ccgccctctc ctcgcgcgc gagtttcagg cagcgctgcg | 13500 |
| tcctgctgcg cacgtgggaa gccctggccc cggccacccc cgcgatgccg cgcgctcccc | 13560 |
| gctgccgagc cgtgcgctcc ctgctgcgca gccactaccg cgaggtgctg ccgctggcca | 13620 |
| cgttcgtgcg gcgcctgggg ccccagggct ggcggctggt gcagcgcggg gacccggcgg | 13680 |
| cttccgcgc gctggtggcc cagtgcctgg tgtgcgtgcc ctgggacgca cggccgcccc | 13740 |
| ccgccgcccc ctccttccgc caggtgggcc tcccgggggt cggcgtccgg ctggggttga | 13800 |
| gggcggccgg ggggaaccag cgacatgcgg agagcagcgc aggcgactca gggcgcttcc | 13860 |
| cccgcaggtg tcctgcctga aggagctggt ggcccgagtg ctgcagaggc tgtgcgagcg | 13920 |
| cggcgcgaag aacgtgctgg ccttcggctt cgcgctgctg gacggggccc gcggggccc | 13980 |
| ccccgaggcc ttcaccacca gcgtgcgcag ctacctgccc aacacggtga ccgacgcact | 14040 |
| gcggggagc ggggcgtggg ggctgctgct gcgccgcgtg ggcgacgacg tgctggttca | 14100 |
| cctgctggca cgctgcgcgc tctttgtgct ggtggctccc agctgcgcct accaggtgtg | 14160 |
| cgggccgccg ctgtaccagc tcggcgctgc cactcaggcc cggccccgc cacacgctag | 14220 |
| tggacccga aggcgtctgg gatgcgaacg ggcctggaac catagcgtca gggaggccgg | 14280 |
| ggtcccctg gcctgccag cccgggtgc gaggaggcgc gggggcagtg ccagccgaag | 14340 |
| tctgccgttg cccaagagc ccaggcgtgg cgctgcccct gagccggagc ggacgcccgt | 14400 |
| tgggcagggg tcctgggccc acccgggcag gacgcgtgga ccgagtgacc gtggtttctg | 14460 |
| tgtggtgtca cctgccagac ccgccgaaga agccacctct ttggagggtg cgctctctgg | 14520 |
| cacgcgccac tcccacccat ccgtgggccg ccagcaccac gcgggccccc catccacatc | 14580 |
| gcggccacca cgtccctggg acacgccttg tccccggtg tacgccgaga ccaagcactt | 14640 |
| cctctactcc tcaggcgaca aggagcagct gcggccctcc ttcctactca gctctctgag | 14700 |
| gcccagcctg actggcgctc ggaggctcgt ggagaccatc tttctgggtt ccaggccctg | 14760 |
| gatgccaggg actccccgca ggttgccccg cctgcccag cgctactggc aaatgcggcc | 14820 |
| cctgtttctg gagctgcttg ggaaccacgc gcagtgcccc tacggggtgc tcctcaagac | 14880 |
| gcactgcccg ctgcgagctg cggtcacccc agcagccggt gtctgtgccc gggagaagcc | 14940 |
| ccagggctct gtggcggccc ccgaggagga ggacacagac cccgtcgcc tggtgcagct | 15000 |
| gctccgccag cacagcagcc cctggcaggt gtacggcttc gtgcgggcct gcctgcgccg | 15060 |
| gctggtgccc ccaggcctct ggggctccag gcacaacgaa cgccgcttcc tcaggaacac | 15120 |
| caagaagttc atctccctgg ggaagcatgc caagctctcg ctgcaggagc tgacgtggaa | 15180 |
| gatgagcgtg cgggactgcg cttggctgcg caggagccca ggtgaggagg tggtggccgt | 15240 |
| cgagggccca ggcccagag ctgaatgcag tagggctca gaaaaggggg caggcagagc | 15300 |

```
cctggtcctc ctgtctccat cgtcacgtgg gcacacgtgg cttttcgctc aggacgtcga    15360
gtggacacgg tgatcgagtc gactcccttt agtgagggtt aattgagctc gcggccgc      15418

<210> SEQ ID NO 2
<211> LENGTH: 7498
<212> TYPE: DNA
<213> ORGANISM: mouse

<400> SEQUENCE: 2
aagcttccag caaaccagtt agagctgagt tgatgctctg aagaagagaa aatgtagaga      60
cggtactgaa caaataatgt ctgggcaaac ctcagacatg aaaatggaag acgtggaaat     120
ccagagaact ctgagggaaa ataaaacaca actccaggtc atcacgggac tcatcaaact     180
gctgaggtgc agcccagag aaaaatctta aaatagccta gaacgatgca tgacacataa      240
agcacagaga agacgaagct gagtctgtct tgtaggaaca acttgagaag acctaaacca     300
ctgcaatgag tgcattctgc taacttagaa tttgctaccc agttcagatc caaaaagggt     360
ttcacaaagt tcaacacaaa acagtagcag gagtggctaa gggggacaca ctgataggaa     420
ttcagagaag tagggaatgc tcatatgggg acattacaaa atgtactttc atgttgctta     480 aatcattta attgtcaacc acatcaagct aaataatgct ttgaggttca taacatttgg      540
agattatgtc tacactagca gagaaggcac caataacatc ccaattgcta gattctcata     600
gaatcatgag tcacaatggc agagacaggt tctgagagtg tgtccttgtt gtaaacagta     660
tgctctacaa actaagttgg ctgcaatatc actaggcagt gttgtcccat aagcaaacta     720
tcacatatgt ggtccagtga tgaccaaagc atcttttagc attttgcaaa tgaagctcaa     780
atcgaatatg actaagctca tgcagtacaa atcaaggta cactgggata gtttaaaaga     840
tacatacttg tactggttag ttttgtgtca gcttgacaca gctggagtta tcacagagaa     900
aagagcttca gttgaggaaa ttcctccatg agatccagct ataggcatt ttctcaatta      960 gtgatcaagg ggggaaggcc ccttgtgggt gggaccatct ctgggctggt agtcttggtt    1020
ctataagaga gcaggctgag caagccagga gaagcaagcc agtaaagaac atccctccat    1080
ggcttctgca tcagctcctg ctccctgacc tgcttgagtt ccagttctaa cttctttcag    1140
tgatgaacag caatgtggaa atgaaagctg aataaaccct ttcctcccca ttttgcttct    1200
tggtcatgat gtttgtgcag gaatagaaac cctgactaag acaatactat aaaccctaaa    1260
agttgtaaac caaacacatg tgtttccatt aagccatcgt agaacaataa gtactcaacc    1320
ccaagtcaca taactataat cccagccttt gaaaaccggg atcaggaatt caaggctagc    1380
ctcatctata tgtaagatta aagcctgttt gggctgcatg agactttgtt tcaaaaaaaa    1440 aaaaaaaaa gcaacaggc aaaacaaac acaagacaag acagatgtaa aatgaaggag       1500
gggtagatgg gtcaagtaga aaatagcata ggaaacgagt caagtataga agaggtggta    1560
gtaaccagat catgcagaag gactcaaggc catctcctca cagtggctta ggtaggcctt    1620
cctctgctct tgagcagggg cagagttgcc gctttaagga ggggatcagt cacctttaag    1680
aactgaaaag ctgaacagtc ttctcaagtc agaagccagt ggcttcatct tacacctctc    1740
ttccttccct tgctactcat attggatctg atgatttgcc caacttggaa gaaacatctc    1800
ttctgaaggt tttcacagac accccatctt tccgagaaag gaccgcatag gctggccatc    1860
cctgtgctta caaaggaat aattaagaaa cttaattcca taagcaaata caaccttttcc   1920 aagccccaag tggatgattt tatccttactg ttttttttata tctcatcaaa taacttccaa   1980
gggctcaaaa atccaaagat gtaaaaaagg aactgagctc tgtttgccaa gccatgagga    2040
```

```
ttaaataatg acattcaaag agattttgt gccctaagta ctttttattg gttttcatag    2100
atggtttaat gtgcaagatg aagcaaacag agatgggagt ggtatcagca tggattaagg    2160
tggcagttgt gagggagggg tactgagaga acaggacaag gtaacctatc taaggagagg    2220
ccaagttggc aagtgccagg gacttctaag cccagaacta gtacacattc cttaggtgct    2280
gtttgggaag tcagggagtc accagccttg ggatctataa agtgcatgg tggcattcac    2340
tcacatactt cctgagctgt tcgatgttga tgaagtcgtg ggtatgagac tgttgtgtca    2400
gtgacaaact atgtaaatga gaatgattgt ttccatcttg accactaaga cgtaaaccgg    2460
ttccagtgat ctccaaacat ggcaagctac agcagagcag cagccccatc cagagccttg    2520
ccctggttct gaatggggga gaatccagtg ggagtcggtt gctgccagca tgttggggta    2580
gaaggctgga gcatgacagg tccccgagga tttcctgctt cctatatggg tagggatact    2640
tgaggtcctc tcttctacct ccttccctgc agggtttata acctctacca ctgtctgtct    2700
ctgggatagc tcctagggtg cagcccctcc ccaaaaaggc ctctccctgg cctcatgtct    2760
ctaagaacag ctttctaaag caggcctgtt acacaaaggc tccctttcc tggcttcatc    2820
gttgctggta gacaacttcc actcgttttc cacttcagtt tcttctactc tgttgttatt    2880
tgattctgat gcttgaaccc aggttgtgt agtcagcaag tgctacccc tccctcctct    2940
tctttgttt tttgaggcag ggtctcattt tgcccaagtg gacctaaatt tcagcatgta    3000
gctggcctgg ttttgaatgc cttctcatcc tgcctctact tcccaagagt agcttacaag    3060
tgtgcaccac catgccccgc gatattctta ttttgagac tgttttctat gctggtttct    3120
ttggggaact acactaaggt agcttacaag tgtgcaccac catgccccgc gatattctta    3180
ttttgagac tgttttctat gctggtttct ttggggaact acactaaggt agcttcattg    3240
ttggcataaa tttctcagtt caggcccata tctcctaagt agcagaacta agcaaatctc    3300
aaacaaaccc ctcaaaaaga ctgatgtcca ctaaacggac ttctaaaata gctcctgtaa    3360
tcctgagcat ttacaaggcg gcagacctcc tataagggag taaatatgaa acgcgcctg    3420
ttcaaatgct aggtcggtgg atagaagcaa tttcctcaga aagctgaagg caccaaaggt    3480
tatatttgtt agcatttcag tgtttgccaa actcagctac agtagagatc acagattccc    3540
tatttcccag agattcaaaa ttcagcagcc cctctctaac tatggctcag agtcgtgtca    3600
ttacatatgc cccaacaaca accccaccc ctatcctacc cccgcctcac acgtgcaagt    3660
actatcacag ttgccaacct agcagagctg ccatcctaag gtcgaggtcg ccgctttggc    3720
tgtgtgcaca ggcaagcgcc ctcacccaat ggccctggcc ttgctatggg tgcgtgagtt    3780
gagatgatgc tctggactct gaggtgaagg ccactgaac agtgaaaaaa gctaacgcag    3840
ggcttttacc tagtccccttt cctttggtgg tgggtgttta cggaacatat ttgggatctg    3900
agtgtatggt cgcaccacaa taaagcctta acctatatag tagaatttca gctgtaatca    3960
ttaagaactg agattgccac cacccacctc actgtctgtg tcaaccacag caggctggag    4020
cagtcagctc aggaacaggc aaaaccttag gtccctccgc ctacctaacc ttcaatacat    4080
caaggatagg cttctttgct tgcccaaacc tcgccccagt ctagaccacc tggggattcc    4140
cagctcaggg cgaaaggaa gcccgagaag cattctgtag agggaaatcc tgcatgagtg    4200
cgccccttt cgttactcca acacatccag caaccactga acttggccgg ggaacacacc    4260
tggtcctcat gcaccagcat tgtgaccatc aacggaaaag tactattgct gcgacccgc    4320
cccttccgct acaacgcttg gtccgcctga atcccgcccc ttcctccgtt cccagcctca    4380
```

```
tcttttttcgt cgtggactct cagtggcctg ggtcctggct gttttctaag cacacccttg    4440
catcttggtt cccgcacgtg ggaggcccat cccggccttg agcacaatga cccgcgctcc    4500
tcgttgcccc gcggtgcgct ctctgctgcg cagccgatac cgggaggtgt ggccgctggc    4560
aacctttgtg cggcgcctgg ggcccgaggg caggcggctt gtgcaacccg gggacccgaa    4620
gatctaccgc actttggttg cccaatgcct agtgtgcatg cactgggct cacagcctcc    4680 acctgccgac cttccttcc accaggtggg cctccaggcg ggatcccat gggtcagggg    4740 cggaaagccg ggaggacgtg ggatagtgcg tctagctcat gtgtcaagac cctcttctcc    4800
ttaccaggtg tcatccctga aagagctggt ggccagggtt gtgcagagac tctgcgagcg    4860
caacgagaga aacgtgctgg cttttggctt tgagctgctt aacgaggcca gaggcgggcc    4920
tcccatggcc ttcactagta gcgtgcgtag ctacttgccc aacactgtta ttgagaccct    4980
gcgtgtcagt ggtgcatgga tgctactgtt gagccgagtg ggcgacgacc tgctggtcta    5040
cctgctggca cactgtgctc tttatcttct ggtgccccc agctgtgcct accaggtgtg    5100
tgggtctccc ctgtaccaaa tttgtgccac cacggatatc tggccctctg tgtccgctag    5160
ttacaggccc acccgacccg tgggcaggaa tttcactaac cttaggttct tacaacagat    5220
caagagcagt agtcgccagg aagcaccgaa acccctggcc ttgccatctc gaggtacaaa    5280
gaggcatctg agtctcacca gtacaagtgt gccttcagct aagaaggcca gatgctatcc    5340
tgtcccgaga gtggaggagg gaccccacag gcaggtgcta ccaaccccat caggcaaatc    5400
atgggtgcca agtcctgctc ggtccccga ggtgcctact gcagagaaag atttgtcttc    5460
taaaggaaag gtgtctgacc tgagtctctc tgggtcggtg tgctgtaaac acaagcccag    5520
ctccacatct ctgctgtcac caccccgcca aaatgccttt cagctcaggc catttattga    5580
gaccagacat ttcctttact ccaggggaga tggccaagag cgtctaaacc cctcattcct    5640
actcagcaac ctccagccta acttgactgg ggccaggaga ctggtggaga tcatctttct    5700
gggctcaagg cctaggacat caggaccact ctgcaggaca caccgtctat cgcgtcgata    5760
ctggcagatg cggcccctgt tccaacagct gctggtgaac catgcagagt gccaatatgt    5820
cagactcctc aggtcacatt gcaggtttcg aacagcaaac caacaggtga cagatgcctt    5880
gaacaccagc ccaccgcacc tcatggattt gctccgcctg cacagcagtc cctggcaggt    5940
atatggtttt cttcgggcct gtctctgcaa ggtggtgtct gctagtctct ggggtaccag    6000
gcacaatgag cgccgcttct ttaagaactt aaagaagttc atctcgttgg ggaaatacgg    6060
caagctatca ctgcaggaac tgatgtgaa gatgaaagta gaggattgcc actggctccg    6120
cagcagcccg ggtgagcatg gctggtctcc agctgaatgc attaggggcc cagaaaaggg    6180
agacaatggg tggcagtaac ccaggtcccc agtggtgtgg tggctttatg cagtccgtgg    6240
ttggatgagt tccatcttat ggtctctgac tccaagctcc ctccagctcg ccttgcacaa    6300
actaagattc ttgtccaagc cctgggcagg ttctcagggc tggggacatt gtggtgaaca    6360
gataagcaga cggggagcat ggtggatagg agttctggca cagtgcacca gagagagtct    6420
ggaagcgcta gtgagagcta atgtaagggc ccgtggttcg ccaaagaatg ataacccgg    6480 actcaaatag tatgccaaag caaggagcat ttcattctgc agaaatcaag catgcaggtg    6540
gggggggggg gttgctctca ttccaagatg gagagacaac caagtataga ttttaagggg    6600
atcgggggcc tttatcttac tccatctcta ggggcattcc attactgggg catggggttg    6660
gaggttggaa actgttaatg gggaggtctg gaaacttgct gccccattgt ccttgcttca    6720
ggctaggtag ctgagtagct tctaatggca ggatagtttc tgactagctg tctaaagtct    6780
```

```
gggggtgtttg ttttttttgtt ttttctagta acttacttgc ctgaacttgc tcagtttta      6840 ggcctggtct  cctggactgc  caatttgaag  cctattaagg  agtcagcctg  tctcactact  6900
ccaggttatc  tataatcccc  ctgtagaacg  gtacctcact  gataacaatg  acagaccaac  6960
ataggaaccc  actatccttg  tggtgcatga  gtttcaaagg  ttcttctggt  cctcccagtg  7020
tgcagatcca  tgcttaagct  atggtcctcc  cagtgtgcag  atccgtgctt  aagctatggt  7080
cttgcagctg  ctcgatctac  aaagggtagg  gtgaacgaag  gaaagataaa  tgaaaaaaaa  7140
aaaactgttt  cctacagtga  agatcgctgc  cccatcttag  ctatgagaag  ggactgggga  7200
gtggagcctg  gtgcataaaa  gaggattgtg  ttacttggaa  ggctgcagag  cctggactcc  7260
tgtgccctcc  ttgcctggtt  ttctgggttt  aatgttgagg  ttggccctct  gtagtcacta  7320
cctgacccct  tcccttcag   ccaaccctcc  ggttacaccc  tgtgcatgta  tggaaggggc  7380
caaacgccct  atcctgctct  ccttcccca   aaattcttag  gatattaaca  acttatgggg  7440
aaaagatggt  agagctatgt  ttacccacca  tgtacttggg  aagctccgaa  gtaagctt    7498
```

ASSAYS FOR TERT PROMOTER MODULATORY AGENTS USING A TELOMERASE STRUCTURAL RNA COMPONENT

CROSS-REFERENCE TO RELATED APPLICATIONS

Pursuant to 35 U.S.C. § 119 (e), this application claims priority to the filing date of U.S. Provisional Patent Application Ser. No. 60/643,649 filed Jan. 12, 2005; the disclosure of which application is herein incorporated by reference.

INTRODUCTION

1. Background of the Invention

Telomeres, which define the ends of chromosomes, consist of short, tandemly repeated DNA sequences loosely conserved in eukaryotes. For example, human telomeres consist of many kilobases of (TTAGGG)n together with various associated proteins. Small amounts of these terminal sequences or telomeric DNA are lost from the tips of the chromosomes during S phase because of incomplete DNA replication. Many human cells progressively lose terminal sequence with cell division, a loss that correlates with the apparent absence of telomerase in these cells. The resulting telomeric shortening has been demonstrated to limit cellular lifespan.

Telomerase is a ribonucleoprotein that synthesizes telomeric DNA. In general, telomerase is made up of two components: (1) an essential structural RNA (TR or TER) (where the human component is referred to in the art as hTR or hTER); and (2) a catalytic protein (telomerase reverse transcriptase or TERT) (where the human component is referred to in the art as hTERT). Telomerase works by recognizing the 3' end of DNA, e.g., telomeres, and adding multiple telomeric repeats to its 3' end with the catalytic protein component, e.g., hTERT, which has polymerase activity, and hTR which serves as the template for nucleotide incorporation. Both the catalytic protein component and the RNA template component are activity-limiting components.

Because of its role in cellular senescence and immortalization, there is much interest in the development of protocols and compositions for regulating telomerase activity. Of particular interest is the development of assays that detect agents that directly regulate the endogenous TERT, and specifically hTERT, promoter, e.g., in a high-throughput format.

2. Literature of Interest

U.S. Pat. Nos. 5,972,605; 6,610,839 and 6,664,046 and published U. S. application Ser. No. 2004/0072787; as well as WO 02/070668; WO 03/016474; WO 03/000916; WO 02/101010; WO 02/090571; WO 02/090570; WO 02/072787; WO 02/070668; WO 02/16658; WO 02/16657; and the references cited therein. Also of interest is Li et al., Rapid Inhibition of Cancer Cell Growth Induced by Lentiviral Delivery and Expression of Mutant-Template Telomerase RNA and Anti-Telomerase Short-interfering RNA," Cancer Res. (Jul. 15, 2004) 64:4833–4840.

SUMMARY OF THE INVENTION

Methods and compositions for assaying an agent for TERT promoter modulatory activity are provided. In the subject methods, an agent is contacted with a cell comprising a mutant telomerase structural RNA component (TR) that results in a detectable phenotype in the presence of telomerase reverse transcriptase (TERT). Also provided are compositions, systems and kits thereof, as well as devices, that find use in practicing the subject methods. The subject invention finds use in assaying agents for TERT promoter modulatory activity, such as in a high throughput format.

Aspects of the invention include methods of determining whether an agent modulates transcription control activity of a TERT promoter, where the method includes:

(a) contacting the agent with a cell that includes a mutant telomerase structural RNA component (TR) that results in a detectable phenotype in the presence of telomerase reverse transcriptase (TERT); and (b) evaluating the cell for the detectable phenotype to determine whether the agent modulates transcription control activity of the TERT promoter nucleic acid. In certain embodiments, TERT promoter nucleic acid is a human TERT promoter nucleic acid. In certain embodiments, the cell comprises an expression cassette that expresses the mutant telomerase structural RNA component (TR). In certain embodiments, the expression cassette is episomally maintained in the cell. In certain embodiments, the expression cassette is chromosomally integrated in the cell. In certain embodiments, the expression cassette is not chromosomally integrated into a chromosome of the cell that includes a TERT coding sequence. In certain embodiments, the cell is a human cell and the expression cassette is not integrated into chromosome 5. In certain embodiments, the detectable phenotype is cell death. In certain embodiments, the cell is a mutant cell that expresses telomerase and the method is a method for determining whether the agent inhibits expression controlled by a TERT promoter nucleic acid. In certain embodiments, the cell is a normal cell and the method is a method of determining whether the agent enhances expression controlled by a TERT promoter nucleic acid. In certain embodiments, the method includes determining the modulatory activity of at least two different agents. In certain embodiments, the method is a high-throughput method. In certain embodiments, the agent is a small molecule.

Additional aspects of the invention include methods of determining whether a small molecule agent can de-repress transcription repression activity of a TERT promoter. In these embodiments, the method includes:

(a) contacting an agent with a cell that includes a mutant telomerase structural RNA component (TR) that results in a detectable phenotype in the presence of telomerase reverse transcriptase (TERT); and (b) evaluating the cell for said detectable phenotype to determine whether said agent de-represses transcription repression activity of said TERT promoter nucleic acid. Variations of this embodiment include those summarized above.

Also provided are systems for determining whether an agent modulates transcription control activity of a TERT promoter, where the systems include:

(a) a cell comprising a mutant telomerase structural RNA component (TR) that results in a detectable phenotype in the presence of telomerase reverse transcriptase (TERT); and (b) said agent.

Also provided are high throughput assay devices that include a cell comprising a mutant telomerase structural RNA component (TR) that results in a detectable phenotype in the presence of telomerase reverse transcriptase (TERT).

DEFINITIONS

As used herein, the term "TERT promoter" includes any TERT genomic sequences capable of driving transcription in a telomerase activity positive cell. Thus, TERT promoters of the invention include without limitation cis-acting transcriptional control elements and regulatory sequences that are involved in regulating or modulating the timing and/or rate of transcription of a TERT gene. For example, the TERT promoter of the invention comprises cis-acting transcriptional control elements, including enhancers, promoters, transcription terminators, origins of replication, chromosomal integration sequences, 5' and 3' untranslated regions, exons and introns, which are involved in transcriptional regulation. These cis-acting sequences typically interact with proteins or other biomolecules to carry out (turn on/off, regulate, modulate, etc.) transcription.

As used herein, the terms "allele" or "allelic sequence" refer to an alternative form of a nucleic acid sequence (i.e., a nucleic acid corresponding to a TERT promoter, particularly, an hTERT promoter). Alleles result from mutations (i.e., changes in the nucleic acid sequence), and can produce differently regulated mRNAs. Common mutational changes that give rise to alleles are generally ascribed to natural deletions, additions, or substitutions of nucleotides. Each of these types of changes may occur alone, in combination with the others, or one or more times within a given gene, chromosome or other cellular nucleic acid. Thus, the term "TERT promoter" includes allelic forms of TERT promoter sequences, i.e., TERT cis-acting transcriptional control elements, including, e.g., the exemplary human and mouse sequences described herein. In alternative embodiments, the TERT promoter sequence comprises TERT sequences 5' (upstream) of the translational start site (ATG). For example, in one embodiment, the hTERT promoter comprises residues 44 to 13545 of SEQ ID NO:01. Other embodiments include sequences starting within about one to 5 nucleotides of a translation start codon (for example in SEQ ID NO:01) and ending at about 50, 100, 150, 200, 250, 500, 1000, 2500 or 13500 nucleotides upstream of the translation start codon. Such embodiments can optionally include other regulatory sequences, such as, exon and/or intron sequences. hTERT promoters of the invention also include sequences substantially identical (as defined herein) to an exemplary hTERT promoter sequence of the invention, having the sequence set forth by SEQ ID NO:01. Similarly, mTERT promoters of the invention also include sequences substantially identical to an exemplary mTERT promoter sequence of the invention, having the sequence set forth by SEQ ID NO:02.

The term "heterologous" when used with reference to portions of a nucleic acid, indicates that the nucleic acid comprises two or more subsequences which are not found in the same relationship to each other in nature. For instance, the nucleic acid is typically recombinantly produced, having two or more sequences from unrelated genes arranged in a manner not found in nature; e.g., a promoter sequence of the invention operably linked to a polypeptide coding sequence that, when operably linked, does not reform the naturally occurring TERT gene. For example, the invention provides recombinant constructs (expression cassettes, vectors, viruses, and the like) comprising various combinations of promoters of the invention, or subsequences thereof, and heterologous coding sequences, many examples of which are described in detail below.

As used herein, "isolated," when referring to a molecule or composition, such as, e.g., an hTERT promoter sequence, means that the molecule or composition is separated from at least one other compound, such as a protein, DNA, RNA, or other contaminants with which it is associated in vivo or in its naturally occurring state. Thus, a nucleic acid sequence is considered isolated when it has been isolated from any other component with which it is naturally associated. An isolated composition can, however, also be substantially pure. An isolated composition can be in a homogeneous state. It can be in a dry or an aqueous solution. Purity and homogeneity can be determined, e.g., using analytical chemistry techniques such as, e.g., polyacrylamide gel electrophoresis (PAGE), agarose gel electrophoresis or high pressure liquid chromatography (HPLC).

As used herein, the terms "nucleic acid" and "polynucleotide" are used interchangeably, and include oligonucleotides (i.e., short polynucleotides). They also refer to synthetic and/or non-naturally occurring nucleic acids (i.e., comprising nucleic acid analogues or modified backbone residues or linkages). The terms also refer to deoxyribonucleotide or ribonucleotide oligonucleotides in either single-or double-stranded form. The terms encompass nucleic acids containing known analogues of natural nucleotides. The term also encompasses nucleic acid-like structures with synthetic backbones. DNA backbone analogues provided by the invention include phosphodiester, phosphorothioate, phosphorodithioate, methyl-phosphonate, phosphoramidate, alkyl phosphotriester, sulfamate, 3'-thioacetal, methylene (methylimino), 3'-N-carbamate, morpholino carbamate, and peptide nucleic acids (PNAs); see Oligonucleotides and Analogues, a Practical Approach, edited by F. Eckstein, IRL Press at Oxford University Press (1991); Antisense Strategies, Annals of the New York Academy of Sciences, Volume 600, Eds. Baserga and Denhardt (NTYAS 1992); Milligan (1993) J. Med. Chem. 36:1923–1937; Antisense Research and Applications (1993, CRC Press). PNAs contain non-ionic backbones, such as N-(2-aminoethyl) glycine units. Phosphorothioate linkages are described in WO 97/03211; WO 96/39154; Mata (1997) Toxicol. Appl. Pharmacol. 144:189–197. Other synthetic backbones encompassed by the term include methyl-phosphonate linkages or alternating methylphosphonate and phosphodiester linkages (Strauss-Soukup (1997) Biochemistry 36:8692–8698), and benzyl-phosphonate linkages (Samstag (1996) Antisense Nucleic Acid Drug Dev 6:153–156).

As used herein, the term "operably linked" refers to a functional relationship between two or more nucleic acid (e.g., DNA) segments. Typically, it refers to the functional relationship of a transcriptional regulatory sequence to a transcribed sequence. For example, a promoter sequence is operably linked to a coding sequence if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

As used herein, "recombinant" refers to a polynucleotide synthesized or otherwise manipulated in vitro (e.g., "recombinant polynucleotide"), to methods of using recombinant polynucleotides to produce gene products in cells or other biological systems, or to a polypeptide ("recombinant protein") encoded by a recombinant polynucleotide. "Recombinant means" also encompass the ligation of nucleic acids having coding or promoter sequences from different sources into an expression cassette or vector for expression of, e.g., a fusion protein; or, inducible, constitutive expression of a protein (i.e., a TERT promoter of the invention operably linked to a heterologous nucleotide, such as a polypeptide coding sequence).

As used herein, the "sequence" of a gene (unless specifically stated otherwise) or nucleic acid refers to the order of nucleotides in the polynucleotide, including either or both strands of a double-stranded DNA molecule, e.g., the sequence of both the coding strand and its complement, or of a single-stranded nucleic acid molecule. For example, in alternative embodiments, the TERT promoter of the invention comprises untranscribed, untranslated, and intronic TERT sequences, e.g., as set forth in the exemplary SEQ ID NO:01 and SEQ ID NO:02.

As used herein, the term "transcribable sequence" refers to any sequence which, when operably linked to a cis-acting transcriptional control element, e.g., a promoter, and when placed in the appropriate conditions, is capable of being transcribed to generate RNA, e.g., messenger RNA (mRNA).

The term "assessing" includes any form of measurement, and includes determining if an element is present or not. The terms "determining", "measuring", "evaluating", "assessing" and "assaying" are used interchangeably and include quantitative and qualitative determinations. Assessing may be relative or absolute. "Assessing the presence of" includes determining the amount of something present, and/or determining whether it is present or absent. As used herein, the terms "determining," "measuring," and "assessing," and "assaying" are used interchangeably and include both quantitative and qualitative determinations.

The terms "identical" or percent "identity," in the context of two or more nucleic acids or polypeptide sequences, refer to two or more sequences or subsequences that are the same or have a specified percentage of nucleotides (or amino acid residues) that are the same, when compared and aligned for maximum correspondence over a comparison window, as measured using one of the following sequence comparison algorithms or by manual alignment and visual inspection. This definition also refers to the complement of a sequence. For example, in alternative embodiments, nucleic acids within the scope of the invention include those with a nucleotide sequence identity that is at least about 60%, at least about 75–80%, about 90%, and about 95% of the exemplary TERT promoter sequence set forth in SEQ ID NO:01 (including residues 44 to 13544 of SEQ ID NO:01) or SEQ ID NO:02. Two sequences with these levels of identity are "substantially identical." Thus, if a sequence has the requisite sequence identity to a TERT promoter sequence or subsequence of the invention, it also is a TERT promoter sequence within the scope of the invention. Preferably, the percent identity exists over a region of the sequence that is at least about 25 nucleotides in length, more preferably over a region that is at least about 50–100 nucleotides in length.

For sequence comparison, typically one sequence acts as a reference sequence, to which test sequences are compared. When using a sequence comparison algorithms test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identity for the test sequence(s) relative to the reference sequence, based on the designated or default program parameters. A "comparison window", as used herein, includes reference to a segment of any one of the number of contiguous positions selected from the group consisting of from 25 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Natl. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., supra).

One example of a useful algorithm is PILEUP. PILEUP creates a multiple sequence alignment from a group of related sequences using progressive, pairwise alignments to show relationship and percent sequence identity. It also plots a tree or dendrogram showing the clustering relationships used to create the alignment. PILEUP uses a simplification of the progressive alignment method of Feng & Doolittle, J. Mol. Evol. 35:351–360 (1987). The method used is similar to the method described by Higgins & Sharp, CABIOS 5:151–153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence (e.g., a TERT promoter sequence of the invention as set forth by. e.g., SEQ ID NO:01 or SEQ ID NO:02) is compared to another sequence to determine the percent sequence identity relationship (i.e., that the second sequence is substantially identical and within the scope of the invention) using the following parameters: default gap weight (3.00), default gap length weight (0.10), and weighted end gaps. PILEUP can be obtained from the GCG sequence analysis software package, e.g., version 7.0 (Devereaux (1984) Nuc. Acids Res. 12:387–395).

Another example of algorithm that is suitable for determining percent sequence identity (i.e., substantial similarity or identity) is the BLAST algorithm, which is described in Altschul (1990) J. Mol. Biol. 215:403–410. Software for performing BLAST analyses is publicly available through the National Center for Biotechnology Information (see webpage [http:] followed by [//www] followed by [.ncbi.nlm.nih] followed by [.gov/]). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul (1990) supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. In one embodiment, to determine if a nucleic acid sequence is within the scope of the invention, the BLASTN program (for nucleotide sequences) is used incorporating as defaults a wordlength (W) of 11, an expectation (E) of 10, M=5, N=4, and a comparison of both strands. For amino acid sequences, the BLASTP program uses as default parameters a wordlength (W) of 3, an expectation (E) of 10, and the BLOSUM62 scoring matrix (see, e.g., Henikoff (1989) Proc. Natl. Acad. Sci. USA 89:10915).

The BLAST algorithm also performs a statistical analysis of the similarity between two sequences (see, e.g., Karlin (1993) Proc. Nat'l. Acad. Sci. USA 90:5873–5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

DESCRIPTION OF THE SPECIFIC EMBODIMENTS

Methods and compositions for assaying an agent for TERT promoter modulatory activity are provided. In the subject methods, an agent is contacted with a cell comprising a mutant telomerase structural RNA component (TR) that results in a detectable phenotype in the presence of telomerase reverse transcriptase (TERT). Also provided are compositions, systems and kits thereof, as well as devices, that find use in practicing the subject methods. The subject invention finds use in assaying agents for TERT promoter modulatory activity, such as in a high throughput format.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Methods recited herein may be carried out in any order of the recited events which is logically possible, as well as the recited order of events.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications mentioned herein are incorporated herein by reference to disclose and describe the methods and/or materials in connection with which the publications are cited. It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

In further describing the invention, the subject methods are described first in greater detail, followed by a review of representative applications in which the subject methods find use, as well as a discussion of representative systems and kits that find use in practicing the subject methods.

Methods

As summarized above, the subject invention provides methods of determining whether an agent has TERT promoter modulatory activity. An agent is considered to have TERT promoter modulatory activity if its interaction with a TERT promoter causes a change in transcription activity, e.g., level (for example, in terms of transcribed copies of a coding sequence for a given period of time) of a nucleic acid sequence (e.g., a transcribable sequence, such as the coding sequence for TERT) operably linked to the promoter, e.g., as compared to a control (e.g., the transcription activity of an analogous TERT promoter/reporter nucleic acid construct not contacted with the agent of interest). The change that is observed may be an increase or decrease of transcription of the operably linked nucleic acid, e.g., TERT coding sequence. In other words, the agent may enhance or inhibit transcription of the nucleic acid sequence operably linked to the TERT promoter. By enhance is meant that the expression level of the operably linked reporter nucleic acid sequence is increased by at least about 2 fold, usually by at least about 5 fold and sometimes by at least 25, 50, 100 fold and in particular about 300 fold or higher, as compared to a control, i.e., expression from an analogous or identical expression system that is not contacted with the agent in question. Alternatively, in cases where expression of the operably linked nucleic acid is so low that it is undetectable, expression of the operably linked nucleic acid is considered to be enhanced if expression is increased to a level that is easily detectable. By inhibit is meant that the expression level of the operably linked nucleic acid sequence is decreased by at least about 2 fold, usually by at least about 5 fold and sometimes by at least 25, 50, 100 fold and in particular about 300 fold or higher, as compared to a control, i.e., expression from an analogous or identical expression system that is not contacted with the agent in question. Alternatively, in cases where expression of the operably linked nucleic acid is detectable, expression of the operably linked nucleic acid is considered to be inhibited if expression is decreased to a level that is not detectable.

In practicing the subject methods, an agent to be tested or assayed for TERT promoter modulatory activity (sometimes referred to herein as a candidate agent) is contacted with a cell that includes a mutant (i.e., modified) telomerase structural RNA component (TR) that results in a detectable phenotype in the presence of telomerase reverse transcriptase (TERT).

Depending on the particular assay, the cell (also referred to herein as the target cell or test cell) with which the agent is contacted during practice of the subject methods may be a normal cell that provides wild type conditions, e.g., a cell that normally lacks telomerase activity, e.g., an MRC5 cell, etc.; or the cell may be mutant cell in which telomerase activity is present, e.g., a cancerous cell. In representative embodiments, the cell is a mammalian cell, where mammalian cells of interest include, but are not limited to: murine, porcine, ovine, equine, rat, ungulates, dog, cat, monkey, and human cells, and the like. In many embodiments, the cell will be a human cell.

A feature of the cells employed in the subject methods is that they include a modified telomerase RNA (TR) component, i.e., a modified TR component. By "modified" is meant that the RNA component differs by at least one base as compared to the corresponding wild-type RNA component present in the cells of the organism from which the test cell was originally obtained. As such, the modified TR component is also properly referred to as a mutant TR component. For example, where the test cell is a mouse cell, the cell includes a modified TR component as compared to the wild-type mouse TR (i.e., mTR) component. Likewise, where the test cell is a human cell, the cell includes a modified TR component as compared to the wild type human TR (i.e., hTR) component. Wild type sequences of TR components as well as the sequences of DNAs encoding the same are known for multiple species, including but not limited to: human, mouse, rat, hamster, cow, etc. See e.g., U.S. Pat. Nos. 6,013,468 and 5,876,979, the disclosures of which are herein incorporated by reference. As indicated above, the sequence of the modified TR component present in the test cells employed in the subject invention differs from the corresponding wild type TR component of the test cell by at least one base, where the number of bases that differ may vary. As such, sequence identity between the modified and corresponding TR component will be less than 100% (as determined using an alignment program, such as an alignment program specified above), where the sequence identity may be less than about 98%, less than about 95%, less than about 90%, less than about 85% etc in certain embodiments.

In certain representative embodiments, the modified TR component is a modified hTR component. In certain of these representative embodiments, the modified hTR component differs from the sequence of the wild type hTR component, as described above. The sequence of the wild-type hTR component for this embodiment is deposited with Genbank and has been assigned an accession no. of NR_001566.

A feature of the modified TR component present in the test cells employed in the subject methods is that the modified TR component imparts a detectable phenotype to the cell in the presence of telomerase reverse transcriptase (TERT). In other words, when TERT is present in the cell along with the modified TR component, the cell has a detectable phenotype that is attributable to the presence of these two components. The detectable phenotype may vary, where representative phenotypes include, but are not limited to: cell death; cell growth/proliferation; cell morphology; the production of new telomere sequences; changes in levels of telomere binding proteins; the presence or absence of binding proteins, e.g., transcriptions factors, that recognize new telomere sequences; changes in gene expression factors (e.g., resulting from presence of new telomere sequences and use of transcription factors as a result thereof, which modulates expression of other gene products); presence of restriction sites in new telomere sequences; changes in fluorescence polarization of the TR component (e.g., when bound to TERT); presence of a reporter gene; presence of a reporter sequence (e.g., directly or indirectly detectable) in a newly synthesized telomere sequence; detection of a TR/TERT complex, either directly or indirectly; and the like.

In representative embodiments, the modified TR component is one that causes cell death (e.g., via apoptosis) in the presence of telomerase. A number of different such modified TR components have been reported in the literature, including, but not limited to, those reported in: Feng et al, Science (1995) 269(5228):1236–41, Kim et al., Proc. Nat'l Acad. Sci. USA (2001) 98: 7982–7; Marusic et al., Mol. Cell Biol. (1997) 17:6394–401; and Li et al., Cancer Res. (2004) 64: 4833–4840.

As the test cell employed in the subject assays comprises a modified TR component. In certain embodiments, an expression cassette that includes a coding sequence for the modified TR component operably linked to suitable promoter is present in the cell.

In certain embodiments, the expression cassette is present on a vector that is episomally (i.e., extrachomosomally) maintained in the host cell. Expression vectors of interest generally contain a promoter that is recognized by the host organism and is operably linked to the coding sequence for the modified TR component. Promoters are untranslated sequences located upstream (5') to the start codon of a structural gene (generally within about 100 to 1000 bp) that control the transcription and translation of particular nucleic acid sequence to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. A large number of promoters recognized by a variety of potential host cells are well known. Both a native promoter sequence, e.g., the promoter sequence operably linked to the wild type TR coding sequence, and many heterologous promoters may be used to direct expression of the coding sequence for the modified TR component.

Transcription from vectors in mammalian cells may be controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter, PGK (phosphoglycerate kinase), or an immunoglobulin promoter, from heat-shock promoters, provided such promoters are compatible with the host cell systems. The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. Also of interest are promoters for snRNAs, e.g. U1 and U6.

Transcription by higher eukaryotes is often increased by inserting an enhancer sequence into the vector. Enhancers are cis-acting elements of DNA, usually about from 10 to 300 bp, which act on a promoter to increase its transcription. Enhancers are relatively orientation and position independent, having been found 5' and 3' to the transcription unit, within an intron, as well as within the coding sequence itself. Many enhancer sequences are now known from mammalian genes (globin, elastase, albumin, a-fetoprotein, and insulin). Typically, however, one will use an enhancer from a eukaryotic cell virus. Examples include the SV40 enhancer on the late side of the replication origin, the cytomegalovirus early promoter enhancer, the polyoma enhancer on the late side of the replication origin, and adenovirus enhancers. The enhancer may be spliced into the expression vector at a position 5' or 3' to the coding sequence, but is preferably located at a site 5' from the promoter.

Expression vectors used in eukaryotic host cells may also contain sequences necessary for the termination of transcription and for stabilizing the mRNA. Such sequences are commonly available from the 5' and, occasionally 3', untranslated regions of eukaryotic or viral DNAs or cDNAs.

In certain embodiments, the expression cassette may be genomically integrated in the target cell, i.e., integrated onto a chromosome of the target cell. A variety of integrating vectors and methodologies for using the same are known in the art. For such embodiments, the expression cassette may be placed into a vector that is suitable for use in integrating the expression cassette into the target cell genome, where representative vectors include, but are not limited to: plasmid DNA vectors, retroviral vectors; adeno-associated vectors, adenoviral vectors, double stranded DNA vectors, etc. For example, viral vector delivery vehicles may be employed to integrate an expression cassette into a target cell genome. A variety of viral vector delivery vehicles are known to those of skill in the art and include, but are not limited to: adenovirus, herpesvirus, lentivirus, vaccinia virus and adeno-associated virus (AAV).

In representative embodiments where the expression cassette encoding the modified TR component is chromosomally integrated and a stable clone of a cell containing this integration is isolated, clones containing integrations into the same chromosome that includes the TERT coding sequence are excluded. For example, where the target cell is a human cell, since the TERT coding sequence is present on Chromosome 5, the modified TR expression cassette is integrated into a chromosome other than Chromosome 5. In cases where the modified TR is chromosomally integrated and used as a pool (i.e., no clonal isolation), then it is not possible to exclude integrations into chromosome 5.

For vector construction, any convenient method may be employed. Construction of suitable vectors containing one or more of the above-listed components may employ standard ligation techniques. Isolated plasmids or DNA fragments are cleaved, tailored, and re-ligated in the form desired to generate the plasmids required. For analysis to confirm correct sequences in plasmids constructed, the ligation mixtures are used to transform host cells, and successful transformants selected by ampicillin or tetracycline resistance where appropriate. Plasmids from the transformants are prepared, analyzed by restriction endonuclease digestion, and/or sequenced.

Yet another feature of certain embodiments of the subject invention is that the target cell is one in which the native TERT gene is present, where by TERT gene is meant the TERT coding sequences as well as transcription control sequences, e.g., promoters, etc. In certain embodiments where the cell is a human cell, the cell includes the native hTERT gene. Yet another feature of certain embodiments of the invention is that the test cell lacks a functional gene for wild type TR, such that wild-type TR is not present in the test cell. In certain embodiments, wild-type TR is present.

In practicing the subject methods, the target cell, as described above, is contacted with the candidate agent whose activity is to be tested. Contact of the candidate agent is achieved using any convenient protocol, such as introducing the agent into cell culture medium in which the target cell is present, etc.

The conditions under which the cell and the candidate agent are contacted may vary depending on the nature of the assay and the nature of the candidate agent modulatory activity to be determined. For example, where the assay is employed to screen candidate agents for TERT promoter de-repression activity, i.e., activation activity, the conditions under which the expression system and the agent are contacted are generally wild type conditions, where the conditions may be described as an environment in which, in the absence of the candidate agent, TERT expression is repressed.

Alternatively, where the assay is employed to screen candidate agents for TERT promoter repression activity, i.e., inhibition activity, the conditions under which the cell and the agent are contacted are generally mutant conditions, where the conditions may be described as an environment in which, in the absence of the candidate agent, TERT expression occurs. Such conditions may be found in target cells that constitutively express TERT, e.g., cancerous cells.

Following contact of the candidate agent and the target cell, the phenotype of cell is evaluated or assessed to determine the promoter modulatory activity of the candidate agent. This step of assessing or evaluating the phenotype of the cell will necessarily vary depending on the nature of the phenotype that is induced by the presence of both TERT and the modified TR component in the cell. This step of the subject methods may include either a qualitative or quantitative evaluation of the phenotype, and may or may not include use of one or more reference or controls, as may be desired.

In certain embodiments, the cell is assayed for cell-death or apoptosis. Any convenient apoptosis assay may be employed, including but not limited to, those described in: (Note: Feng at all describes altered telomeres but no apoptosis assay) Kim et al., Proc. Nat'l Acad. Sci. USA (2001) 98: 7982–7; Marusic et al., Mol. Cell Biol. (1997) 17:6394–401; and Li et al., Cancer Res. (2004) 64: 4833–4840.

Where the phenotype to be evaluated is cell death, any convenient assay for such a phenotype may be employed, where a number of different such assays are known to those of skill in the art. Specific representative assays of interest are reviewed in greater detail below.

In certain embodiments, the assay can be one the employs a mixed population of test and non-test cells, where the assay looks at changes in the proportion of each type of cell in the population as an indication of the presence of cell death in the test cell. For example, a first population of test cells may be produced by transfecting the mutant TR expression construct into normal cells along with reporter construct, e.g., a gene expressing the Green Fluorescent Protein, where the reporter construct may be on the same vector as, or a different vector from, the mutant hTR expression construct, e.g., on the plasmid or on a separate plasmid. A second population of control cells may be transfected with a second reporter construct distinct from the first, e.g., a reporter construct that expresses a non-Green Fluorescent Protein, such as Red, Yellow, Blue, etc. In certain embodiments, the second reporter construct may be on the same vector as a wild type hTR expression construct, e.g., on the plasmid. As a result, two different populations of cells, e.g., cell lines, are produced, where the cell lines are identical except that the first test cell line expresses mutant hTR and a first reporter molecule, e.g., GFP, while the second control cell line expresses wild type hTR and a second reporter molecule, e.g., RFP. Following production of the test and control cell populations, a mixed population is produced in which the test and control cells are mixed together in known amounts, e.g., in equal amounts, such that a mixture of cells is produced in which the proportion of test and control cells is known. Application of a test compound to such a mixed population provides for a ready determination of whether the compound has a modulatory effect on TERT promoter activity. For example, if a compound has no effect on the cells (e.g., it does not activate telomerase expression) then both test and control cells should grow normally and the ratio of signal from the first and second reporter construct, e.g., ratio of GFP to RFP should remain constant, e.g. 1 where the population includes equal amounts of cells. Alternatively, if a compound activates hTERT expression and incorporation of the mutant hTR negatively effects the health of the cells, then the ratio of GFP to RFP should decrease relative to the starting ratio, e.g., to less than 1, such as to less then 0.1. In these representative embodiments, if a compound is toxic to all cells, then the ratio of GFP to RFP should remain 1, but the total fluorescent signal should be significantly less since neither cell grew.

Other assays for dead or live cells that can be included in at least some of the assays described above include: Caspase assays for the presence of apoptosis (such as Caspase 3 and 7 activity measurement: Caspase-Glo 3/7 Assay, cat.# G8092 (Promega); Caspase 8 activity measurement: Caspase-Glo 8 Assay, cat.# G8202 (Promega); Caspase 9 activity measurement: Caspase-Glo 9 Assay, cat.# G8212 (Promega); etc.); viability and proliferation assays, such as ATPlite, cell viability homogenous assay cat.# 6016947 (PerkinElmer), etc.; cell death detection assays, such as Cell Death Detection ELISAPLUS cat.# 1 920 685 (Roche Applied Science); Propidium Iodide assay (MTG, Inc. Product number M0795); etc.

In yet other embodiments, the assay employed may include molecular probing for new telomere sequences. Such embodiments include those situations where the presence of new telomere sequences is used as the indication of TERT promoter activity. The presence of new telomere sequences may be detected using any of a number of different protocols, e.g., by hybridization, PCR, FRET, or antibody, etc. In yet other embodiments, the evaluation step may include probing for lack of telomere binding proteins. In yet other embodiments, the evaluation step may include probing for binding proteins (e.g., transcription factors) that recognize new telomere sequences. In yet other embodiments, the evaluation step may include assaying for altered regulation of genes whose transcription factors are recruited by the new telomere sequences, if present, where such recruitments results in a modulation of the expression pattern of one or more additional genes. In certain embodiments, the evaluation step includes a step of probing for reporter sequences that are present in a newly synthesized telomere sequence, where representative reporter sequences of interest include restriction sites. In certain embodiments, cells are evaluated for an alteration of fluorescence polarization of the TR component, e.g., mutant hTR (or hTER), when bound to telomerase, e.g., (hTERT). In certain embodiments, cells are assayed for the presence of a reporter gene (e.g., where the template region of hTR is altered to express a reporter gene, such as luciferase (or adenovirus VA RNA sequence), where the new telomere sequence would contain repeats of the luciferase gene and synthesis of new telomeres would be detected by luciferase activity. In certain embodiments, evaluation includes a FISH assay. In certain embodiments, evaluating includes assaying for virus integration into an integration site within a new telomere sequence. In certain embodiments, evaluating includes assaying for site-specific recombination of a reporter gene (e.g., Luciferase) into a recombination site within a new telomere sequence. In certain embodiments, evaluating includes detection of a reporter sequence in a new telomere sequence, e.g., via an engineered Zinc Finger Protein. In certain embodiments, evaluating includes assaying directly for complex formation of the TR and TERT components, e.g., via FRET using antibody to hTERT and oligo to mutant template of hTR. The above assays are merely representative.

In certain embodiments, the subject methods are performed in a high throughput (HT) format. In the subject HT embodiments of the subject invention, a plurality of different compounds are simultaneously tested. By simultaneously tested is meant that each of the compounds in the plurality are tested at substantially the same time. Thus, at least some, if not all, of the compounds in the plurality are assayed for their effects in parallel. The number of compounds in the plurality that are simultaneously tested is typically at least about 10, where in certain embodiments the number may be at least about 100 or at least about 1000, where the number of compounds tested may be higher. In general, the number of compounds that are tested simultaneously in the subject HT methods ranges from about 10 to 10,000, usually from about 100 to 10,000 and in certain embodiments from about 1000 to 5000. A variety of high throughput screening assays for determining the activity of candidate agent are known in the art and are readily adapted to the present invention, including those described in e.g., Schultz (1998) Bioorg Med Chem Lett 8:2409–2414; Weller (1997) Mol Divers. 3:61–70; Fernandes (1998) Curr Opin Chem Biol 2:597–603; Sittampalam (1997) Curr Opin Chem Biol 1:384–91; as well as those described in published U.S. application Ser. No. 20040072787 and issued U.S. Pat. No. 6,127,133; the disclosures of which are herein incorporated by reference.

Testing of a candidate agent according to the invention as described above readily determines whether or not an agent has TERT promoter modulatory activity. As mentioned above, an agent is considered to have TERT promoter modulatory activity if its interaction with TERT promoter causes a change in transcription activity, e.g., level (for example, in terms of transcribed copies for a given period of time), of a nucleic acid sequence (i.e., transcribable sequence) operably linked to the promoter, e.g., as compared to a control (e.g., the transcription activity of an analogous TERT promoter/reporter nucleic acid construct not contacted with the agent of interest). The change that is observed may be an increase or decrease of TERT transcription. In other words, the agent may enhance or inhibit transcription of TERT. By enhance is meant that the expression level of TERT is increased by at least about 2 fold, usually by at least about 5 fold and sometimes by at least 25, 50, 100 fold and in particular about 300 fold or higher, as compared to a control, i.e., expression from an analogous or identical expression system that is not contacted with the agent in question. Alternatively, in cases where expression of TERT is so low that it is undetectable, expression of TERT is considered to be enhanced if expression is increased to a level that is easily detectable. By inhibit is meant that the expression level of the TERT is decreased by at least about 2 fold, usually by at least about 5 fold and sometimes by at least 25, 50, 100 fold and in particular about 300 fold or higher, as compared to a control, i.e., expression from an analogous or identical expression system that is not contacted with the agent in question.

Utility

A variety of different candidate agents may be screened by the above methods. Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

The subject assays find use in any application where it is desired to determine whether a candidate agent has TERT promoter modulatory activity. Specifically, the subject assays find use in applications where one wishes to determine whether an agent has TERT promoter repressor activity and in applications where one wishes to determine whether an agent has TERT promoter activator or enhancer activity. In representative embodiments, the methods provide for identification of agents which have human TERT promoter modulatory activity.

Agents identified in the above screening assays that inhibit repression of TERT transcription find use in the methods of enhancement of TERT expression, e.g., in the treatment of disease conditions, in research applications, etc., where representative specific applications include those described in United States Published Applications: 20030211965; 20030171326; 20030104420; 20030050264; and 20020193289; the disclosures of which are herein incorporated by reference. Alternatively, agents identified in the above screening assays that enhance repression find use in applications where inhibition of TERT expression is desired, e.g., in the treatment of disease conditions characterized by the presence of unwanted TERT expression, such as cancer and other diseases characterized by the presence of unwanted cellular proliferation, where such methods are described in, for example, U.S. Pat. Nos. 5,645,986; 5,656, 638; 5,703,116; 5,760,062; 5,767,278; 5,770,613; and 5,863, 936; the disclosures of which are herein incorporated by reference.

Kits

Also provided are kits that find use in practicing the subject methods, as described above. For example, in some embodiments, kits for practicing the subject methods include at least a test cell as described above, or elements for constructing the same, e.g., expression vectors, etc. Furthermore, additional reagents that are required or desired in the protocol to be practiced with the kit components may be present, which additional reagents include, but are not limited to: aqueous mediums, culture mediums, and the like. The kits may also include reference or control elements, e.g., that provide calibration signals or values for use in assessing the observed signal generated by an assay performed with the kit components. The kit components may be present in separate containers, or one or more of the components may be present in the same container, where the containers may be storage containers and/or containers that are employed during the assay for which the kit is designed.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

Systems

Also provided are systems that find use in practicing the subject methods, as described above. For example, in some embodiments, systems for practicing the subject methods include at least a test cell as described above. Furthermore, additional reagents that are required or desired in the protocol to be practiced with the system components may be present, which additional reagents include, but are not limited to: aqueous mediums, culture mediums, and the like. The systems may also include reference or control elements, e.g., that provide calibration signals or values for use in assessing the observed signal generated by an assay performed with the system components. The systems generally also include one or more candidate agents.

Devices

Also provided are high throughput (HT) devices that find use in practicing the subject methods, particularly HT embodiments thereof. The high throughput devices may have any convenient configuration, and generally include a plurality of two or more fluid containment elements in which assays can take place, agent administration elements and signal detection elements. For example, representative HT devices of the subject invention include a plate or substrate having a plurality of fluid-containing wells, reagent-adding equipment responsive to a computer for adding reagent, e.g., candidate agent, to the wells, measurement equipment for measuring at least one attribute of the sample or cells contained by the wells (e.g., for phenotype evaluation) and moving equipment which is responsive to the computer for aligning one of the wells first with the reagent-adding component, then with the measurement device, as further described in U.S. Pat. No. 6,127,133, the disclosure of which is herein incorporated by reference. Also of interest are the devices described in U.S. Pat. Nos. 6,468,736 and 5,989,835; as well as U.S. Provisional Application Ser. No. 60/618,484; the disclosures of which are herein incorporated by reference. A feature of the HT devices of the present invention is that they include in at least one fluid containment element containing a target cell as described above.

It is evident from the above results and discussion that the subject invention provides for greatly improved assays for determining the TERT promoter modulatory activity of a candidate agent. A particularly important advantage provided by certain embodiments of the subject invention is that the modulatory activity of the candidate agent is assessed on a native TERT gene present in a cell. Accordingly, the subject invention represents a significant contribution to the art.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of determining whether an agent modulates transcription control activity of a telomerase reverse transcriptase (TERT) promoter nucleic acid operatively linked to a nucleic acid encoding a TERT, said method comprising:
   (a) contacting said agent with a cell, wherein said cell comprises:
      i) said TERT promoter nucleic acid operatively linked to said nucleic acid encoding said TERT; and
      ii) a mutant telomerase structural RNA component (TR) that imparts a detectable phenotype to said cell when said encoded TERT is expressed in said cell; and
   (b) evaluating said cell for said detectable phenotype to determine whether said agent modulates transcription control activity of said TERT promoter nucleic acid, wherein said detectable phenotype is at least one of cell death and the presence of a reporter sequence of said mutant TR in a newly synthesized telomere sequence.

2. The method according to claim 1, wherein said TERT promoter nucleic acid is a human TERT promoter nucleic acid.

3. The method according to claim 1, wherein said cell comprises an expression cassette that expresses said mutant TR.

4. The method according to claim 3, wherein said expression cassette is episomally maintained in said cell.

5. The method according to claim 3, wherein said expression cassette is chromosomally integrated in said cell.

6. The method according to claim 5, wherein said expression cassette is not chromosomally integrated into a chromosome that includes a TERT coding sequence.

7. The method according to claim 6, wherein said cell is a human cell and said expression cassette is not integrated into chromosome 5.

8. The method according to claim 1, wherein said cell is a mutant cell that expresses telomerase and said method is a method for determining whether said agent inhibits expression controlled by said TERT promoter nucleic acid.

9. The method according to claim 1, wherein said cell is a normal cell and said method is a method of determining whether said agent enhances expression controlled by said TERT promoter nucleic acid.

10. The method according to claim 1, wherein said method comprises determining said modulatory transcriptional control activity of at least two different agents.

11. The method according to claim 10, wherein said method is a high-throughput method.

12. The method according to claim 1, wherein said agent is a small molecule.

13. A method of determining whether an agent can derepress transcription repression activity of a TERT promoter nucleic acid operatively linked to a nucleic acid encoding a TERT, said method comprising:
   (a) contacting said agent with a cell, wherein said cell comprises:
      i) said TERT promoter nucleic acid operatively linked to said nucleic acid encoding said TERT; and
      ii) a mutant TR that imparts a detectable phenotype to said cell when said encoded TERT is expressed in said cell; and
   (b) evaluating said cell for said detectable phenotype to determine whether said agent derepresses transcription repression activity of said TERT promoter nucleic acid, wherein said detectable phenotype is at least one of cell death and the presence of a reporter sequence of said mutant TR in a newly synthesized telomere sequence.

14. The method according to claim 13, wherein said cell is a human cell.

15. The method according to claim 14, wherein said TERT promoter nucleic acid is a human TERT promoter nucleic acid.

16. The method according to claim 13, wherein said cell comprises an expression cassette that expresses said mutant TR.

17. The method according to claim 16, wherein said expression cassette is episomally maintained in said cell.

18. The method according to claim 16, wherein said expression cassette is chromosomally integrated in said cell.

19. The method according to claim 18, wherein said expression cassette is not chromosomally integrated into a chromosome that includes a TERT coding sequence.

20. The method according to claim 13, wherein said method comprises determining said transcription derepression activity of at least two different agents.

21. The method according to claim 20, wherein said method is a high-throughput method.

22. The method according to claim 13, wherein said agent is a small molecule.

* * * * *